United States Patent [19]

Sweeney et al.

[11] Patent Number: 4,929,232
[45] Date of Patent: May 29, 1990

[54] SYRINGE HAVING TAMPER EVIDENCE FEATURES

[75] Inventors: Niall Sweeney, Rutherford; Sandor Gyure, West Orange, both of N.J.

[73] Assignee: Becton, Dickinson and Company, Franklin Lakes, N.J.

[21] Appl. No.: 330,676

[22] Filed: Mar. 30, 1989

[51] Int. Cl.$^5$ ............................................. A61M 5/00
[52] U.S. Cl. .................................................. 604/111
[58] Field of Search ............... 604/111, 220, 242, 110, 604/218, 243

[56] References Cited

U.S. PATENT DOCUMENTS

| | | |
|---|---|---|
| 2,371,086 | 3/1945 | Watson et al. |
| 4,007,740 | 2/1977 | Owen. |
| 4,300,678 | 11/1981 | Gyure et al. ......................... 206/364 |
| 4,475,903 | 10/1984 | Steenhuisen et al. ............... 604/111 |
| 4,832,695 | 5/1989 | Rosenberg et al. .................. 604/111 |

*Primary Examiner*—John D. Yasko
*Attorney, Agent, or Firm*—John L. Voellmicke

[57] ABSTRACT

A syringe having tamper evidence features includes a barrel having a chamber for retaining fluid, an open proximal end, and a distal end having a passsageway therethrough in fluid communication with the chamber. A needle shield having a longitudinal axis, a distal end and an open proximal end slidably engages the distal end of the barrel covering the passageway. The shield includes an outwardly projecting shield lug having a cam surface. A collar having an annular side wall, an open proximal end and a distal end having an aperture therethrough, is adjacent to the distal end of the barrel with the needle shield projecting distally through the aperture. The apreture is sized so that the proximal end of the needle shield cannot pass therethrough. The collar includes an inwardly projecting lug having a follower surface for contacting the cam surface. The cam surface and the follower surface being configured so that rotational force applied to the needle shield around the longitudinal axis causes the cam surface to contact the follower surface to apply a force to the follower surface. Securement means is provided for releasably holding the collar adjacent to the barrel. The securement means is positioned so that the force applied to the follower surface can disengage the securement means allowing the collar to move and allowing the needle shield to be removed from the barrel.

18 Claims, 8 Drawing Sheets

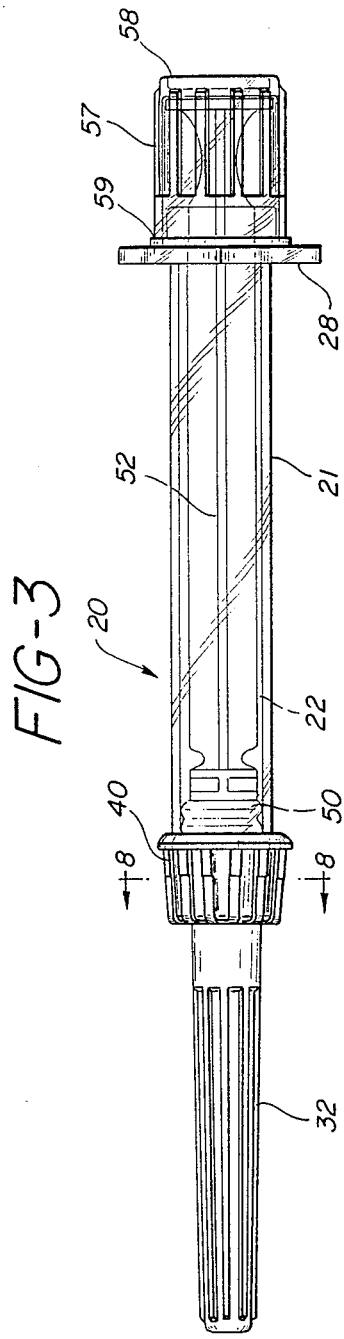
FIG-3
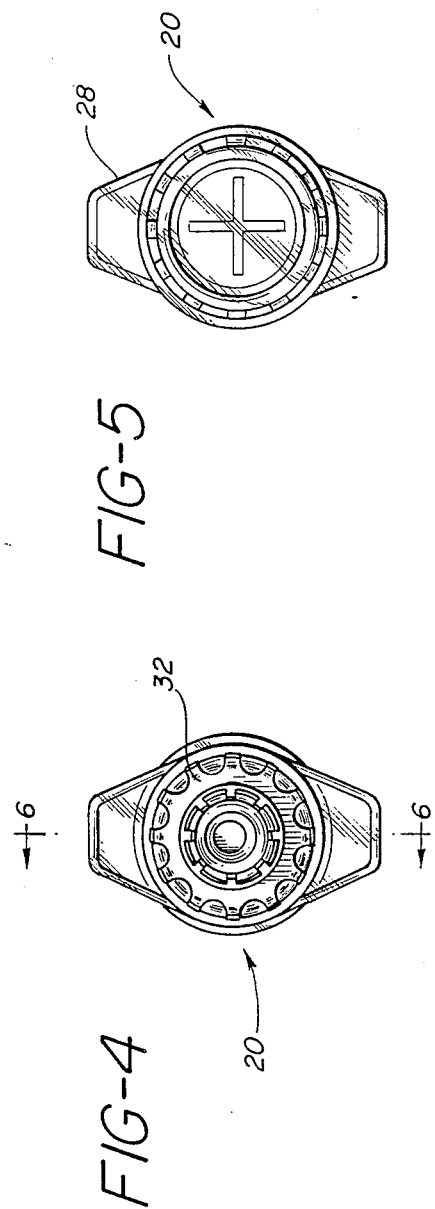
FIG-5
FIG-4

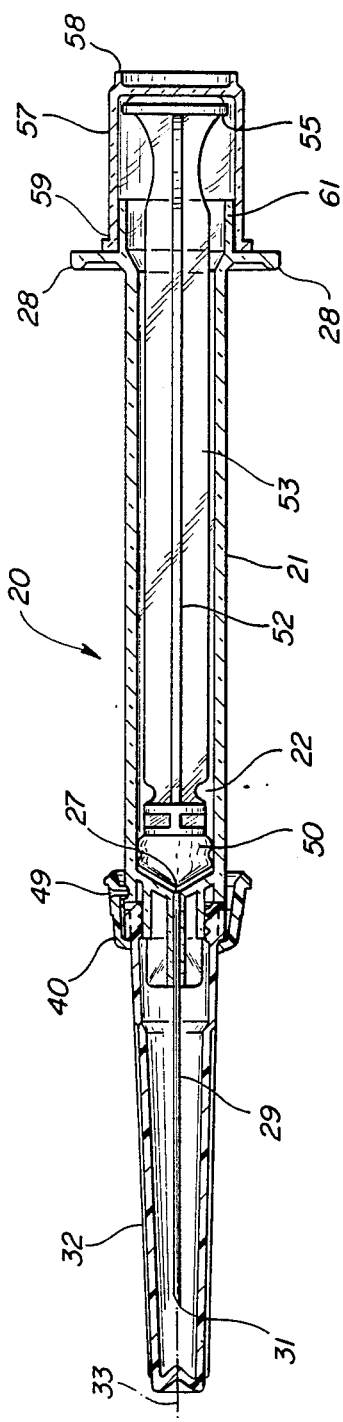

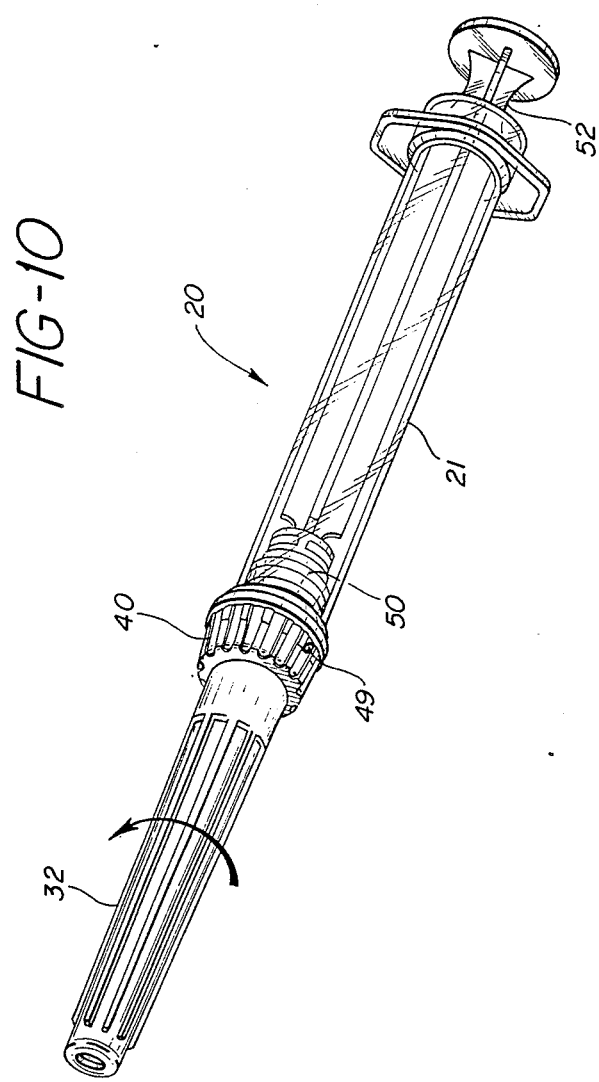

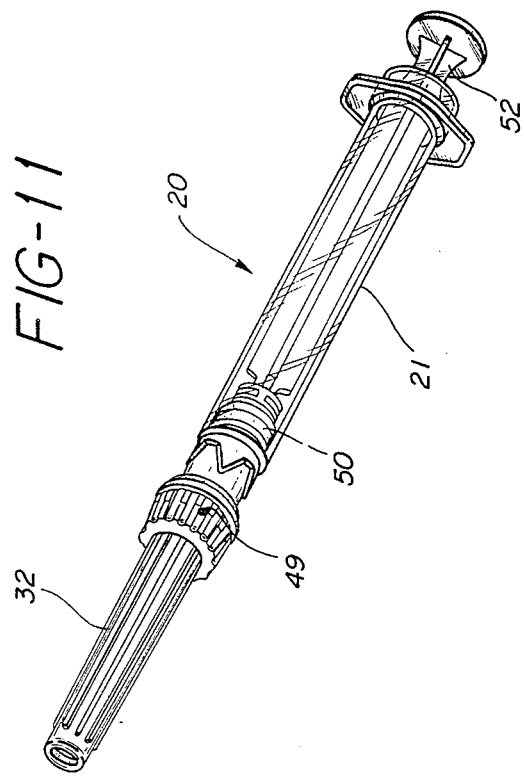

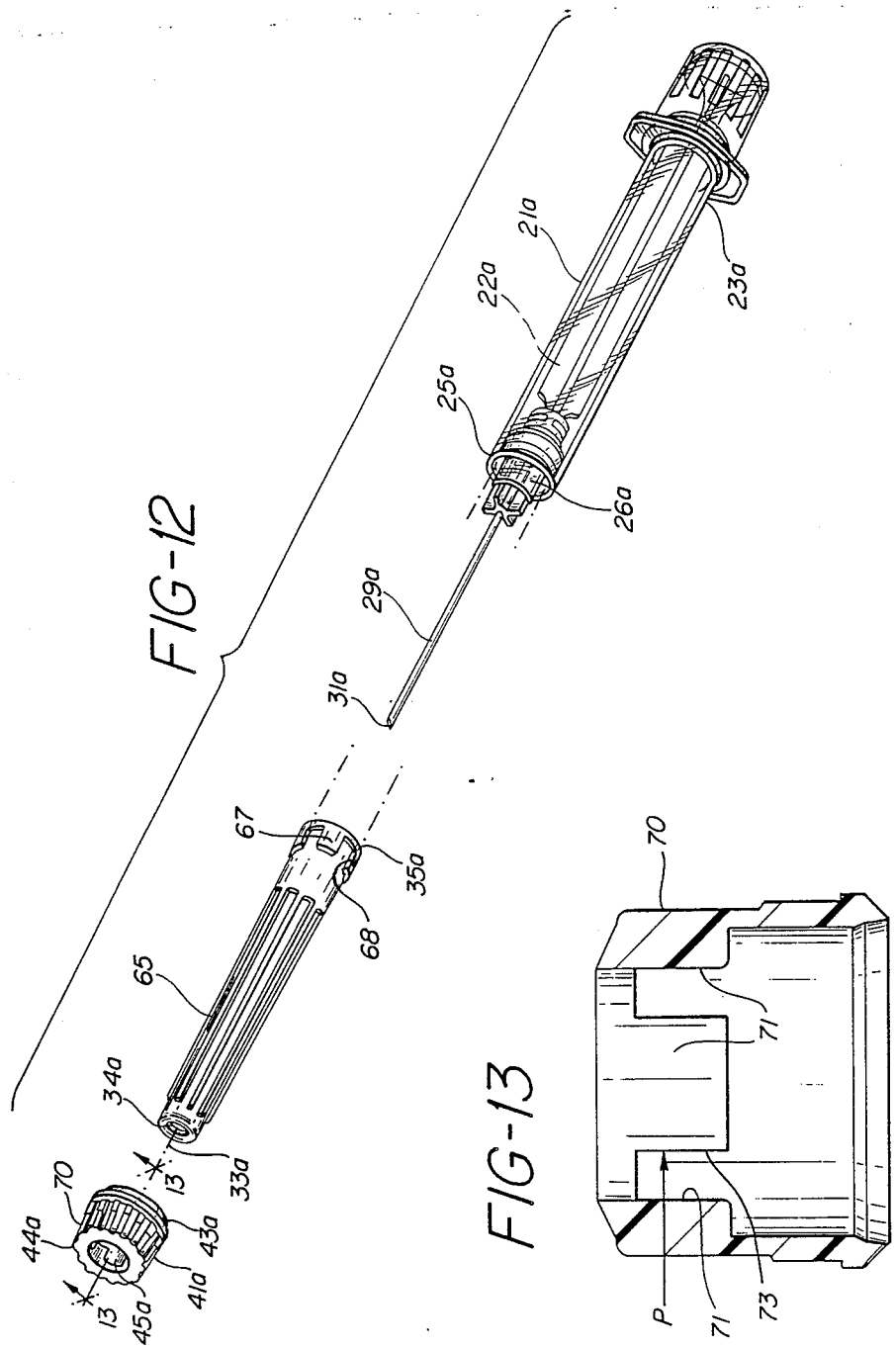

SYRINGE HAVING TAMPER EVIDENCE FEATURES

BACKGROUND OF THE INVENTION

1. Field of the Invention

The present invention relates to syringes and more particularly concerns disposable syringes having tamper evidence features.

2. Description of Related Information

Generally speaking, a hypodermic syringe consists of a cylindrical barrel, most commonly made of plastic or glass, with the distal end containing a hypodermic needle or adapted to be connected to a hypodermic needle, and a proximal end adapted to receive a stopper and plunger rod assembly. The distal end of the barrel or the needle assembly usually includes the needle shield which removably covers the needle to prevent damage to the needle before use and to prevent accidental needle sticks.

In United States and throughout the world, the multiple use of hypodermic syringe products, which are intended for single use only, is instrumental in drug abuse and more particularly in the transfer of contagious diseases. In addition, drug abusers have been known to remove all or part of the contents of a prefilled hypodermic syringe and replace the missing medicament with water. The needle shield is then carefully replaced so that the subsequent user is not aware that the syringe has been previously used to inject the medication contained therein and/or that the contents have been diluted with water. The subsequent recipient of the injection from such a syringe may suffer the consequences of ineffective drug therapy and may also be infected if the needle was previously used to inject medication.

To remedy drug abuse, drug misuse and contamination problems associated with tampering with syringe assemblies by removing and replacing the needle shield, U.S. Pat. No. 2,371,086 to Watson et al. teaches a hypodermic syringe assembly having a glass needle shield with a zone of reduced diameter and reduced wall thickness that may be sheared to remove the distal end of the needle shield. The device of Watson et al. is also deficient in that it does not allow reshielding because there are no structural elements which will interact to hold the severed portion of the needle shield to the syringe after it is removed. Also in narrow diameter of Watson's needle shield at the point of reduced thickness makes reshielding needle shield, if it were possible, a difficult and possible dangerous process.

U.S. Pat. No. 4,007,740 to Owen also teaches a cannula covering having a frangible section which must be broken to expose the sharpened distal tip of the cannula. The frangible portion which appears only slightly larger in diameter than the needle cannula, once broken, provides evidence of possible tampering or prior use. The narrow diameter of Owen's needle shield in the area of the frangible zone makes it difficult to reshield and increases the probability of the user accidentally sticking himself during the act or reshielding. Also, Owen does not provide structure to hold the severed portion of the needle shield on after reshielding. Accordingly, the needle shield may easily fall off the needle exposing the sharpened needle tip to possibly injure or infect a person handling the used syringe.

U.S. Pat. No. 4,300,678 to Gyure et al. also teaches a needle shield which, at its base is permanently connected to the syringe barrel. The shield also includes a frangible portion adapted to be ruptured so that a first distal portion of the shield is removable from the second portion which remains connected to the barrel. Gyure et al. like Watson et al. and Owen do not provide structure for securely retaining the needle shield on the syringe assembly after use and reshielding. In addition, the normal act of removing the needle shield is to hold the syringe in one hand and the needle shield in the other hand and twist and remove the needle shield. The syringe of the '678 patent, in the alternative embodiment of FIGS. 4 and 5, requires an additional first step of peeling the frangible portion away from the syringe at which point the needle shield may again be gasped in the normal manner for removal of the needle shield.

In U.S. Pat. No. 4,475,903 to Steenhuisen et al. teaches a syringe which is provided with a sleeve of shrinkable plastic material which is shrunk around the needle connection and the barrel. Steenhuisen et al. teach the placement of the shrinkable plastic sleeve so that after the sleeve is broken and the needle guard removed it will be substantially impossible to place the needle guard back to its original position because the broken portion of the sleeve prevents its return.

Although the prior art provides teaching with respect to syringe assemblies having removable needle shields, there is still a need for a syringe having tamper evidence features which does not destroy the needle shield and which allows the option of safe effective reshielding of the needle after injection using the needle shield. There is also a need for syringe assemblies having tamper evidence features which allow removal of the needle shield by holding the syringe barrel in one hand and the needle shield in the other wherein the tamper evidence means can be severed with reasonable rotational or twisting force and in a manner which will not encourage accidental needle sticks, such as by pulling apart the needle shield away from the syringe barrel to sever the tamper evidence means. There is also a need for a separable tamper evidence indicator that may be removed and destroyed at the time of injection while still allowing the option of reshielding but not reassembly of the syringe in its original form because of the missing tamper evidence indicator.

SUMMARY OF THE INVENTION

A syringe assembly having tamper evidence features of the present invention includes a barrel having a chamber for retaining fluid, an open proximal end, and a distal end having a passageway therethrough in fluid communication with the chamber. An elongate, hollow needle shield having a longitudinal axis, a distal end and an open proximal end is slidably engaged with the distal end of the barrel, covering the passageway. The shield includes an outwardly projecting shield lug having a cam surface thereon. A collar having an annular side wall, an open proximal end and a distal end having an aperture therethrough is adjacent to the distal end of the barrel. The needle shield projects distally through the aperture in the collar. The collar aperture is sized so that the proximal end of the needle shield cannot pass therethrough. The collar includes an inwardly projecting lug having a follower surface thereon for contacting the cam surface of the needle shield. The cam surface and the follower surface are configured so that rotational force applied to the needle shield along the longitudinal axis causes the cam surface to contact the follower surface to apply a force to the follower surface. Securement means is provided for releasably holding the collar adjacent to the barrel. The securement means is positioned so that force applied to said follower surface through said cam surface can disengage the securement means allowing the collar to move and allowing the needle shield to be removed from the barrel.

In accordance with the preferred embodiment of the present invention, a syringe having tamper evidence features includes an elongate barrel having a chamber for retaining fluid, an open proximal end, and a distal end. A tip extends from the distal end of the barrel. The tip includes a passageway therethrough in fluid communication with the chamber. A needle cannula having a lumen therethrough extends outwardly from the distal end of the barrel so that the lumen is in fluid communication with the passageway. An elongate, hollow needle shield having a longitudinal axis, a closed distal end and an open proximal end slidably engages the tip and covers the needle cannula. The shield includes an outwardly projecting shield lug having a cam surface. A cup-shaped collar having an annular side wall, an open proximal end and a distal end having an aperture therethrough is adjacent to the proximal end of the needle shield. The proximal end of the collar is adjacent to the distal end of the barrel. The needle shield projects distally through the aperture which is sized and shaped so that the proximal end of the needle shield cannot pass therethrough. The collar includes an inwardly projecting lug having a follower surface for contacting the cam surface of the needle shield. The cam surface and the follower surface are configured so that rotational force applied to the needle shield around a longitudinal axis of the needle shield causes the cam surface to contact the follower surface to apply force to the follower surface. This applied force includes an axial component for forcing the collar away from the barrel toward the distal end of the needle shield. Securement means is provided for releasably holding the collar adjacent to the barrel. The securement means is positioned so that the force applied to the follower surface through the cam surface can disengage the securement means allowing the cam surface of the needle shield to move the collar toward the distal end of the needle shield and for allowing the needle shield to be removed from the barrel. A stopper is slidably positioned in fluid-tight engagement inside the barrel. The stopper is capable of moving fluid from the chamber through the passageway upon its movement toward the distal end of the barrel. The stopper is capable of facilitating the drawing of fluid into the chamber through the passageway upon its movement away from the distal end. A plunger rod having an elongate body portion engages the stopper to facilitate operation of the stopper. The body portion of the plunger rod extends outwardly from the proximal open end of the barrel to form a syringe assembly.

The present invention provides a simple, straight-forward, reliable, easily fabricated syringe having a tamper evident collar which is disconnectable from the syringe barrel by application of a rotational force to the needle shield wherein interaction between the needle shield and the collar causes the rotational force to apply an axial force to the collar forcing the collar toward the distal end of the needle shield away from the syringe barrel. The movement of said collar providing evidence of prior use or tampering.

BRIEF DESCRIPTION OF THE DRAWINGS

FIG. 3 is a side elevation view of the syringe of FIG. 1;

FIG. 4 is a side elevation view of the distal end of the syringe of FIG. 3;

FIG. 5 is a side elevation view of the proximal end of the syringe of FIG. 3;

FIG. 6 is a partial cross-sectional view of the syringe of FIG. 4 taken along lines 6—6;

FIG. 10 is a perspective view of the syringe of the instant invention with barrel cap removed illustrating the forces required to move the tamper evident collar;

FIG. 11 is a perspective view of the syringe of FIG. 10 with collar shown with tamper evident collar displaced in the distal direction;

FIG. 12 is an exploded perspective view illustrating an alternative embodiment of the syringe of the present invention with the collar and needle shield positioned for assembly; and FIG. 13 is an enlarged cross-sectional view of the collar of FIG. 12 taken along lines 13—13.

DETAILED DESCRIPTION

Figure 1:
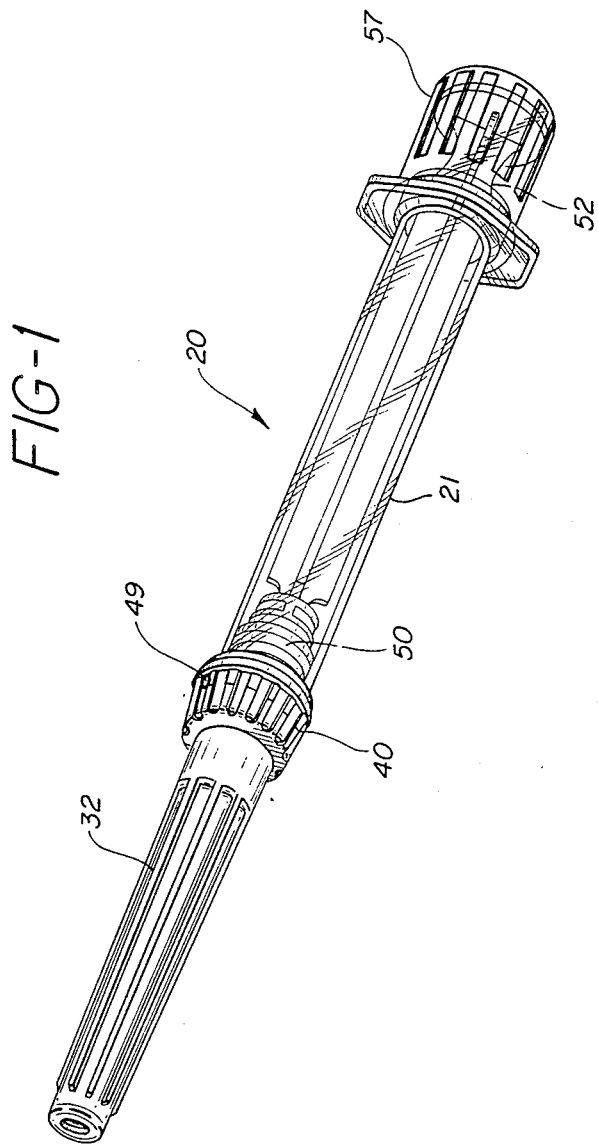
FIG. 1 is a perspective view of the syringe of the present invention.
Figure 2:
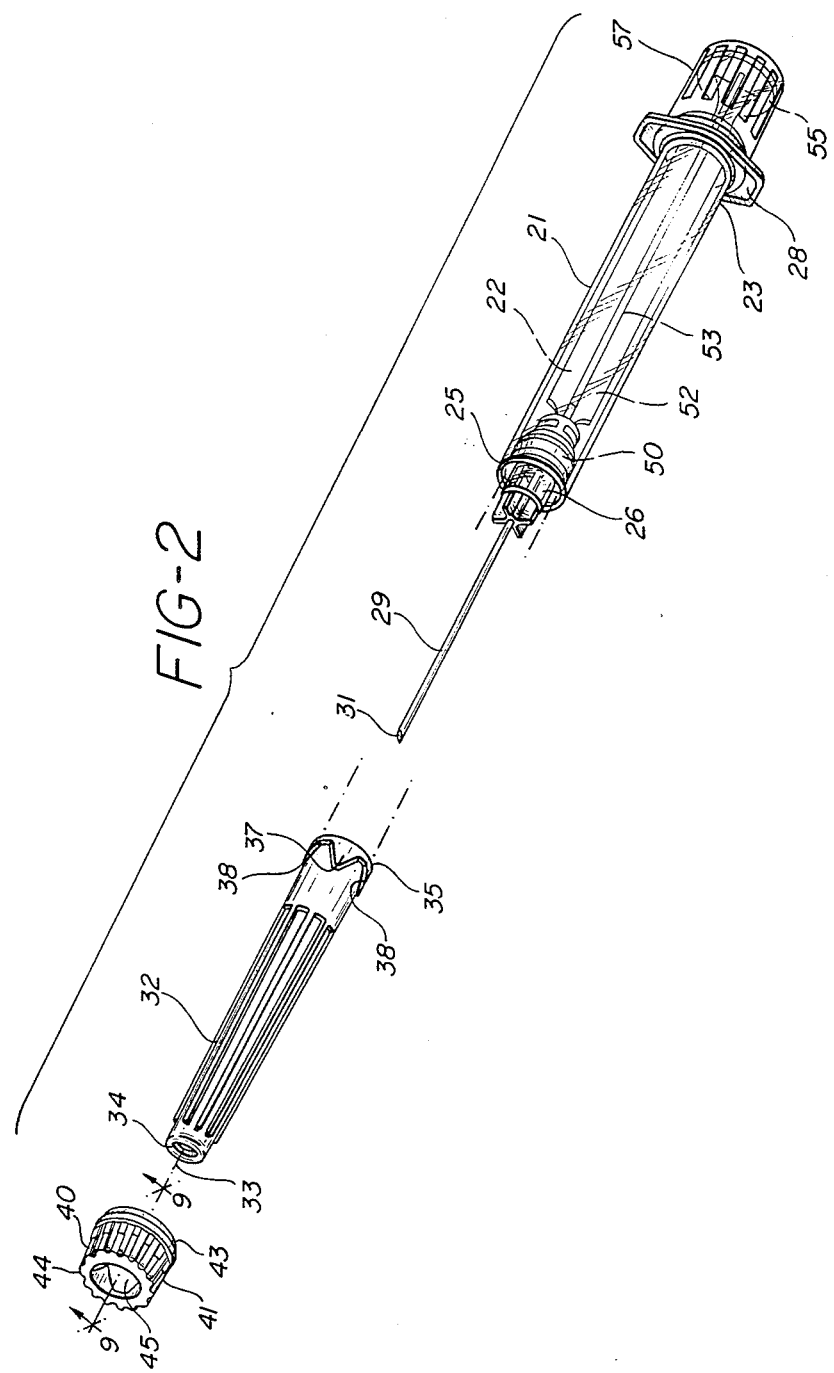
FIG. 2 is an exploded perspective view illustrating the syringe of the present invention with the collar and needle shield positioned for assembly.
Figure 7:
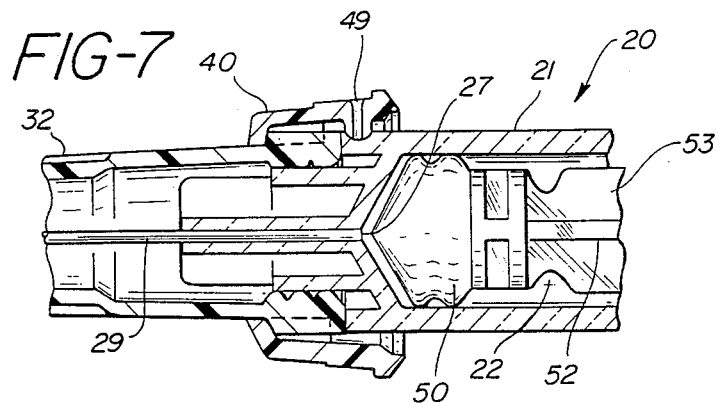
FIG. 7 is an enlarged partial view of the syringe of FIG. 6 taken in the area of the collar.
Figure 8:
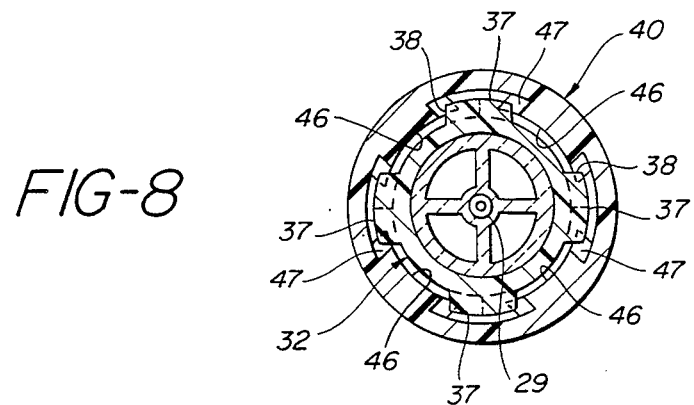
FIG. 8 is an enlarged cross-sectional view of the syringe of FIG. 3 taken along lines 8—8.

While this invention is satisfied by embodiments in many different forms, there is shown in the drawings and will herein be described in detail a preferred embodiment of the invention with the understanding that the present disclosure is to be considered exemplary of the principles of the invention and is not intended to limit the invention to the embodiment illustrated. The scope of the invention will be measured by the appended claims and their equivalents.

Adverting to FIGS. 1 through 9, a syringe assembly 20, having tamper evidence features, includes an elongate barrel 21 having a chamber 22 for retaining fluid. Barrel 21 includes open proximal end 23 and distal end 25. A tip 26 extends from the distal end of the barrel and includes a passageway 27 therethrough in fluid communication with chamber 22. A needle cannula 29 having a sharpened distal tip 31 and a lumen therethrough in fluid communication with passageway 27 projects outwardly from distal barrel end 25. The syringe of the instant invention is preferably used with a cannula which is attached to the distal end of the barrel using adhesives or other suitable means. It will be apparent to one skilled in the art that the instant syringe may be used in applications not requiring a needle attached directly to the syringe such as a syringe having a removable needle and hub assembly or in other applications not requiring a needle, and that the attached cannula of the preferred embodiment is only one of these many possibilities.

For the purposes of the description of the present invention, the term "distal end" is meant to refer to the end furthest from the person holding the syringe, whereas the term "proximal end" is meant to refer to the end closest to the holder of the syringe.

An elongate hollow needle shield 32 having a longitudinal axis 33, a closed distal end 34 and an open proximal end 35 slidably engages tip 26 covering needle cannula 29. Needle shield 32 also includes outwardly projecting shield lugs 37 having cam surface 38. In this preferred embodiment there are four equally spaced shield lugs. Each shield lug is preferably triangularly shaped having a planar cam surface. Although a needle shield having only one shield lug is within the purview of the instant invention multiple shield lugs, as will be explained in more detail hereinafter, are preferred.

A cup-shaped collar 40 having an annular side wall 41, an open proximal end 43 and a distal end 44 with an aperture 45 therethrough is positioned so that distal end 44 is adjacent to the needle shield and proximal collar end 43 is adjacent to distal end 25 of barrel 21. The needle shield projects distally through aperture 45. Aperture 45 is sized and shaped so that the proximal end of the needle shield cannot pass therethrough. Collar 40 also preferably includes four equally spaced inwardly projecting lugs 46, each lug having a follower surface 47 for contacting cam surface 38 of the needle shield lugs. Although a collar having only one inwardly projecting lug is within the purview of the instant invention, a plurality of lugs, as will be explained in more detail hereinafter, are preferred. Also, although other shapes and configurations are within the purview of the instant invention lugs 46 of this embodiment are preferably triangularly shaped having a planar follower surface.

Figure 9:
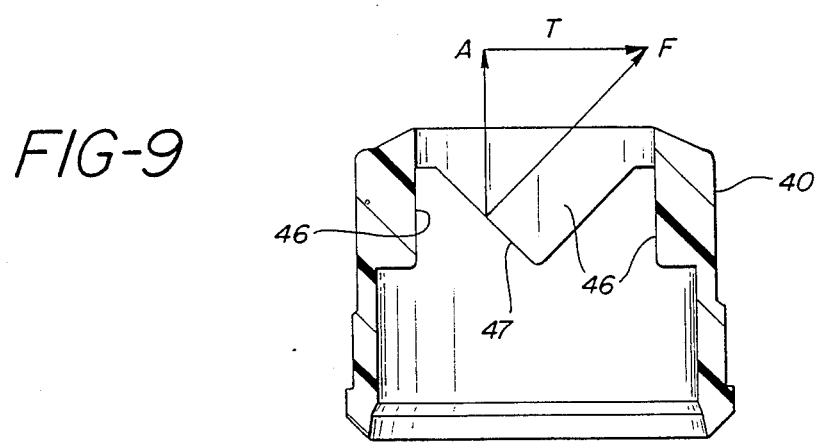
FIG. 9 is an enlarged cross-sectional view of the collar of FIG. 2 taken along lines 9—9.

Cam surface 38 and follower surface 47 are configured so that rotational force applied to needle shield 32 about longitudinal axis 33 causes cam surface 38 to contact follower surface 47 to apply a force F, as illustrated in FIG. 9. Force F has a tangential component T and in this preferred embodiment an axial component A. As will be explained, the elements of the instant syringe assembly allowing rotational force applied to the needle shield to result in an axial force against the collar lug is an important feature of the preferred embodiment of the instant invention.

Securement means for releasably holding the collar adjacent to the barrel is provided. The securement means holds the collar in a fixed position with respect to the barrel. The collar in turn holds the needle shield in a locked position for preventing inadvertent removal thereof. Securement means preferably includes a weld portion wherein a small portion of the collar is attached to the outer surface of the distal end of the barrel through the application of heat energy, ultrasonic energy, adhesive or other suitable means. Ultrasonic welding or heat sealing are preferred along with adhesives such as solvent-type adhesive, UV curable adhesive, two-part epoxy and the like. As will become apparent, it is important that once the securement means is defeated through the use of force that it cannot be reinstated. Accordingly, some contact adhesives may not be desirable for this application. Once defeated the securement means should not be capable of being reinstated to its full strength without the use of similar equipment or adhesives to reestablish the weld portion. The weld portion helps prevent inadvertent removal of the needle shield. The weld portion also provides tamper evidence, warning the user of potential contamination of the syringe assembly when the weld is broken. An important feature of the preferred embodiment of the instant invention is that the weld portion is positioned so that force applied to the follower surface through the cam surface can disengage the weld portion allowing cam surface 38 of the needle shield to move collar 40 distally by virtue of force component A.

It is preferred that collar 40 be dimensioned so that it loosely engages the needle shield and the barrel so that when the weld portion is broken the collar has a tendency to travel along the needle shield and fall off the syringe and is not easily returned to its initial secured position. Also, force component A will tend to propel the collar outwardly providing easily visible evidence of tampering to the syringe user. The collar will also provide evidence that the syringe was not tampered with, if the collar is firmly in place and not moved.

It will be apparent to one skilled in the art that numerous lug shapes, cam surface and follower surface shapes and configurations can be used to convert rotational force applied to the longitudinal axis of the needle shield into a force applied to the collar which in the preferred embodiment has an axial component tending to drive the collar toward the distal end of the needle shield. The art of cam design using curved or flat, curvilinear, or compound curve cam surfaces, and flat or curved, compound curved or curvilinear shaped follower surfaces may be used to achieve the desired required result of an axial and a tangential force component. It is not within the purview of the instant invention to include syringe assemblies wherein rotation of the needle shield does not apply force to the collar necessary to sever or overcome the securement means.

Another feature of the instant invention is that the securement means may be defeated by using only rotational force on the needle shield. This is an important feature since if strong securement means, such as that provided by the weld portion, would have to be severed with axial force, the user will be required to grab the barrel and the needle shield and pull these elements in opposite directions. After the weld portion is broken there may be a tendency for the hands to spring back together causing an inadvertent needle stick. Although the needle would probably still be sterile, the user would have to endure a possibly painful needle stick and the needle would then be contaminated and not suitable for injection into another person.

Still another feature of the instant invention is that the collar may be removed and placed in a separate locked security container or destroyed at the time of injection while still allowing the option of reshielding but not reassembly of the syringe to its original appearance because of the missing collar. Accordingly, the missing collar would be clear evidence of prior use or tampering.

The preferred embodiment also includes a stopper slidably positioned in fluid-tight engagement inside barrel 21. The stopper is capable of moving fluid from chamber 22 through passageway 27 upon its movement toward distal end 25 of the barrel. The stopper is also capable of facilitating the drawing of fluid into the chamber through the passageway upon its movement away from distal end 25 of the barrel. A plunger rod 52 having an elongate body portion 53 engages stopper 50 to facilitate operation of the stopper. Body portion 53 extends outwardly from open proximal end 23 of the barrel. Disc-shaped plunger rod flange 55 is provided as a convenient structure for applying force to the plunger rod with respect to the barrel. A flange 28 is also provided at the proximal end of the barrel to facilitate handling and positioning the syringe assembly and for maintaining the relative position of the barrel with respect to the plunger rod during filling and medication administration.

A cup-shaped cap 57 having a closed proximal end 58 and an open distal end 59 removably engages the proximal end of barrel 21 covering the plunger rod. Cap 57 prevents access to the plunger rod and helps preserve the sterility of the chamber before use. Cap 57 engages cylindrical projection 61 on the barrel in a frictional interference fit. At the time of use the cap may be removed by applying an axial and/or rotational force to the cap while maintaining the position of the barrel. The interface between cylindrical projection 61 and cap 57 and/or the interface between needle shield 32 and tip 26 may be designed to provide a tortuous or labyrinth path to facilitate the use of sterilization procedures using gases such as ethylene oxide. The needle shield and/or the cap may contain an aperture covered by known and commerically available filter materials which will allow the use of gas sterilization processes but include pore sizes which are sufficiently small to prevent the passage of bacteria. A syringe assembly with these features is capable of delivering the sterile injection without the use of additional packaging materials to maintain the sterility of its medication contacting surfaces.

In use, as best illustrated in FIGS. 10 and 11, the syringe assembly of the instant invention is held by the user. At this time the tamper evident collar is manually checked to assure that the securement means, such as weld portion 49, is secure and has not been severed. If the weld portion is not intact the collar will fall off the syringe when the needle shield is oriented downwardly or will easily be removed with a moderate amount of manual force. If the collar is intact the user applies a rotational force along the longitudinal axis of needle shield 32 while holding barrel 21. As described hereinabove, rotation of the needle shield with respect to the barrel causes the cam surface to contact the follower surface to apply a force to the follower surface. The force including its axial component, in the preferred embodiment will sever the weld portion releasing the collar and allowing it to be easily removed from the syringe assembly wherein the needle shield may be easily removed for filling and administering of medication using known sterile techniques.

Referring now to FIGS. 12 and 13, an alternative embodiment of the syringe assembly of the present invention is illustrated. In this alternative embodiment the structure of the syringe assembly is substantially similar to the preferred syringe assembly of FIGS. 1–11. Accordingly, substantially similar components that perform substantially similar functions will be numbered identically to those components of the embodiment of FIGS. 1–11 except a suffix "a" will be used to identify these components in FIGS. 12 and 13.

A syringe assembly having tamper evidence features, includes an elongate barrel 21a having a chamber 22a for retaining fluid. Barrel 21a includes open proximal end 23a and distal end 25a. A tip 26a extends from the distal end of the barrel and includes a passageway therethrough (not shown) in fluid communication with chamber 22a. A needle cannula 29a having a sharpened distal tip 31a and a lumen therethrough in fluid communication with the passageway projects outwardly from distal barrel end 25a.

An elongate hollow needle shield 65 having longitudinal axis 33a, and closed distal end 34a and an open proximal end 35a slidably engages tip 26a covering needle cannula 29a. Needle shield 65 also includes outwardly projecting shield lugs 67 having cam surface 68. In this alternative embodiment there are four equally spaced shield lugs. Each shield lug is rectangularly shaped having a planar cam surface.

A cup-shaped collar 70 having an annular side wall 41a, an open proximal end 43a and a distal end 44a with an aperture 45a therethrough is positioned, when assembled, so that distal end 44a is adjacent to the needle shield and proximal end 43a is adjacent to distal end 25a of barrel 21a. The needle shield projects distally through aperture 45a. Aperture 45a is sized and shaped so that the proximal end of the needle shield cannot pass therethrough. Collar 70 also includes four equally spaced inwardly projecting lugs 71, each having a follower surface 73 for contacting cam surface 68 of the needle shield lugs.

Cam surface 68 and follower surface 73 are configured so that rotational force applied to needle shield 65 about longitudinal axis 33a causes cam surface 68 to contact follower surface 73 to apply a force P, as illustrated in FIG. 13. Force P is substantially tangential to annular side wall 41a and in this embodiment substantially perpendicular to follower surface 73.

Securement means for releasably holding the collar adjacent to the barrel (not illustrated) is provided. The securement means holds the collar in a fixed position with respect to the barrel. The collar in turn holds the needle shield in a fixed position for preventing inadvertent removal thereof. Securement means preferably includes a weld portion wherein a small portion of the collar is attached to the outer surface of the distal end of the barrel through the application of heat energy, ultrasonic energy, adhesive or other suitable means. The weld portion helps prevent inadvertent removal of the needle shield. The weld portion also provides tamper evidence, warning the user of potential contamination of the syringe assembly when the weld is broken. The weld portion is positioned so that if force applied to follower surface 73 through cam surface 68 can disengage the weld portion allowing the cam surface 68 of the needle shield to move the collar rotationally around tip 26a by virtue of force P. Once the weld portion is broken needle shield 65 may be easily removed from tip 26a.

The syringe barrel of the present invention may be constructed of a wide variety of materials with thermoplastic materials such as polypropylene and polyethylene being preferred. Similarly the needle shield, collar, and plunger rod cap are preferably formed of thermoplastic materials such as polypropylene, polyethylene and/or polystyrene. The choice of materials for the collar and the barrel may be influenced by the type of securement means chosen. For example, materials suitable for ultrasonic welding or heat sealing may not be the best choice for securing the collar to the syringe barrel using adhesives. A wide variety of materials such as natural rubber, synthetic rubber and thermoplastic elastomers are suitable for the stopper. It is desirable that the syringe assembly of the present invention be sterile when used. Accordingly, all components used in the syringe barrel should be chosen to withstand the sterilization process being utilized.

Thus, it can be seen that the present invention provides a simple, straight-forward, reliable, easily fabricated, syringe assembly having tamper evidence features including structure which allows disconnecting of a tamper evident collar from a syringe barrel by applying rotational force to the needle shield with respect to the barrel. In the preferred embodiment the interaction between the needle shield and the collar results in an applied force having an axial component to move the collar away from the syringe barrel. The present invention also provides tamper evidence without destroying the needle shield and also allows the option of reshielding of the needle after injection. The present invention also provides the advantage that the collar may be placed in a separate security container or destroyed at the time of injection while still allowing reshielding but not reassembly of the syringe to its original appearance because of the missing collar.

What is claimed is:

1. A syringe assembly having tamper evidence features comprising:
    an elongate barrel having a chamber for retaining fluid, said barrel including an open proximal end and a distal end;
    a tip extending from said distal end of said barrel having a passageway therethrough in fluid communication with said chamber;
    a needle cannula extending outwardly from said distal end, said needle cannula having a lumen therethrough in fluid communication with said passageway;
    an elongate hollow needle shield having a longitudinal axis, a closed distal end and an open proximal end, said shield slidably engaging said tip and covering said needle cannula, said shield having an outwardly projecting shield lug having a cam surface;
    a cup-shaped collar having an annular side wall, an open proximal end and a distal end having an aperture therethrough, said collar proximal end being adjacent to said distal end of said barrel, said needle shield projecting distally through said aperture, said aperture being sized and shaped so that said proximal end of said needle shield cannot pass therethrough, said collar including an inwardly projecting lug having a follower surface for contacting said cam surface of said needle shield, said cam surface and said follower surface being configured so that rotational force applied to said needle shield around said longitudinal axis causes said cam surface to contact said follower surface to apply a force to said follower surface; and
    securement means for releasably holding said collar adjacent to said barrel, said securement means positioned so that force applied to said follower surface through said cam surface can disengage said securement means allowing said cam surface of said needle shield to move said collar and allowing said needle shield to be removed from said barrel.

2. The syringe of claim 1 wherein said cam surface and said follower surface are configured so that rotational force applied to said needle shield around said longitudinal axis causes said force applied to said follower surface to have an axial component for forcing said collar away from said barrel toward said distal end of said needle shield.

3. The syringe assembly of claim 2 wherein said cam surface is planar.

4. The syringe assembly of claim 2 wherein said follower surface is planar.

5. The syringe assembly of claim 2 wherein said collar lug is triangularly shaped.

6. The syringe assembly of claim 2 wherein said needle shield lug is triangularly shaped.

7. The syringe assembly of claim 1 including at least two needle shield lugs and at least two collar lugs positioned so that a rotational force applied to said needle shield causes at least two needle shield lugs to simultaneously engage two collar lugs for applying at least two forces to said collar for disengaging said securement means.

8. The syringe assembly of claim 1 having a plurality of equally spaced needle shield lugs and a plurality of equally spaced collar lugs.

9. The syringe assembly of claim 1 wherein said securement means includes a portion of said collar being attached to a portion of said barrel by a process selected from the group of heat sealing and ultrasonic welding.

10. The syringe assembly of claim 1 wherein said securement means includes adhesive.

11. The syringe assembly of claim 1 further including a stopper slidably positioned in fluid-tight engagement inside said barrel, said stopper capable of moving fluid from said chamber through said passageway upon its movement toward said distal end, said stopper capable of facilitating the drawing of fluid into said chamber through said passageway upon its movement away from said distal end; and
    a plunger rod having an elongate body portion engaging said stopper to facilitate operation of said stopper, said body portion extending outwardly from said proximal end of said barrel to form a syringe assembly.

12. The syringe assembly of claim 11 further including a cup-shaped cap having a closed proximal end and an open distal end removably engaging said proximal end of said barrel portion and covering said plunger rod, said cap preventing access to said plunger rod and helping to preserve the sterility of said chamber before use.

13. The syringe assembly of claim 1 wherein said barrel portion is made of material selected from the group of polyethylene and polypropylene.

14. A syringe assembly having tamper evidence features comprising:
    a barrel having a chamber for retaining fluid, said barrel including an open proximal end and a distal end having a passageway therethrough in fluid communication with said chamber;
    an elongate, hollow needle shield having a longitudinal axis, a distal end and an open proximal end, said shield slidably engaging said distal end of said barrel portion and covering said passageway, said shield having an outwardly projecting shield lug having a cam surface;
    a collar having an annular side wall, an open proximal end and a distal end having an aperture therethrough, said collar proximal end being adjacent to said distal end of said barrel, said needle shield projecting distally through said aperture, said aperture being sized so that said proximal end of said needle shield cannot pass therethrough, said collar including an inwardly projecting lug having a follower surface for contacting said cam surface of said needle shield, said cam surface and said follower surface being configured so that rotational force applied to said needle shield around said longitudinal axis causes said cam surface to contact said follower surface to apply a force to said follower surface; and securement means for releasably holding said collar adjacent to said barrel, said securement means positioned so that said force applied to said follower surface through said cam surface can disengage said securement means allowing said collar to move and allowing said needle shield to be removed from said barrel.

15. A syringe assembly having tamper evidence features comprising:

an elongate barrel having a chamber for retaining fluid, said barrel including an open proximal end and a distal end;

a tip extending from said distal end of said barrel having a passageway therethrough in fluid communication with said chamber;

a needle cannula extending outwardly from said distal end, said needle cannula having a lumen therethrough in fluid communication with said passageway;

an elongate, hollow needle shield having a longitudinal axis, a closed distal end and an open proximal end, said shield slidably engaging said tip and covering said needle cannula, said shield having an outwardly projecting shield lug having a cam surface;

a cup-shaped collar having an annular side wall, an open proximal end and a distal end having an aperture therethrough, said collar distal end being adjacent to said needle shield proximal end and said collar proximal end being adjacent to said distal end of said barrel, said needle shield projecting distally through said aperture, said aperture being sized and shaped so that said proximal end of said needle shield cannot pass therethrough, said collar including an inwardly projecting lug having a follower surface for contacting said cam surface of said needle shield, said cam surface and said follower surface being configured so that rotational force applied to said needle shield around said longitudinal axis causes said cam surface to contact said follower surface to apply a force to said follower surface, said force having an axial component to force said collar away from said barrel toward said distal end of said needle shield;

securement means for releasably holding said collar adjacent to said barrel, said securement means positioned so that force applied to said follower surface through said cam surface can disengage said securement means allowing said cam surface of said needle shield to move said collar toward said distal end of said needle shield and allowing said needle shield to be removed from said barrel;

a stopper slidably positioned in fluid-tight engagement inside said barrel, said stopper capable of moving fluid from said chamber through said passageway upon its movement toward said distal end, said stopper capable of facilitating the drawing of fluid into said chamber through said passageway upon its movement away from said distal end; and a plunger rod having an elongate body portion engaging said stopper to facilitate operation of said stopper, said body portion extending outwardly from said proximal end of said barrel to form a syringe assembly.

16. The syringe assembly of claim 15 including at least two needle shield lugs and at least two collar lugs positioned so that a rotational force applied to said needle shield causes at least two needle shield lugs to simultaneously engage two collar lugs for applying at least two forces to said collar for disengaging said securement means.

17. The syringe assembly of claim 15 having a plurality of equally spaced needle shield lugs and a plurality of equally spaced collar lugs.

18. The syringe assembly of claim 15 further including a cup-shaped cap having a closed proximal end and an open distal end removably engaging said proximal end of said barrel and covering said plunger rod, said cap preventing access to said plunger rod and helping to preserve the sterility of said chamber before use.

* * * * *